(12) United States Patent
Sapiejewski (10) Patent No.: US 6,831,984 B2
(45) Date of Patent: Dec. 14, 2004

(54) NOISE REDUCING (75) Inventor: Roman Sapiejewski, Boston, MA (US)

(73) Assignee: Bose Corporation, Framingham, MA (US)

(*) Notice: Subject to any disclaimer, the term of this patent is extended or adjusted under 35 U.S.C. 154(b) by 280 days.

(21) Appl. No.: 09/886,777

(22) Filed: Jun. 21, 2001

(65) Prior Publication Data

US 2002/0015501 A1 Feb. 7, 2002

Related U.S. Application Data

(63) Continuation of application No. 08/843,985, filed on Apr. 17, 1997, now abandoned.

(51) Int. Cl.[7] .................... A61F 11/06; G10K 11/16; H03B 29/00; H04R 25/00
(52) U.S. Cl. .................... 381/71.6; 381/72; 381/338; 381/371; 181/182
(58) Field of Search .................... 381/71.6, 72, 74, 381/370, 371, 372, 373, FOR 149, 338, 353; D14/205, 206; 181/128, 129, 182

(56) References Cited

U.S. PATENT DOCUMENTS

| 4,160,135 A | 7/1979 | Gorike | 381/372 |
|---|---|---|---|
| 4,644,581 A | 2/1987 | Sapiejewski | 381/74 |
| 4,742,887 A * | 5/1988 | Yamagishi | 181/129 |
| 4,833,719 A | 5/1989 | Carme et al. | 381/71.6 |
| 4,922,542 A | 5/1990 | Sapiejewski | 381/74 |
| 5,610,987 A | 3/1997 | Harley | 381/67 |

FOREIGN PATENT DOCUMENTS

| EP | 0 688 143 A2 | 6/1995 |
|---|---|---|
| EP | 0 688 143 A | 12/1995 |
| GB | 1 379 372 A | 1/1975 |
| GB | 2 000 941 A | 1/1979 |
| JP | 04 227 396 | 8/1992 |
| JP | 04 227 396 A | 8/1992 |
| WO | WO 95/00946 | 1/1995 |
| WO | 95/00 946 A | 1/1995 |

* cited by examiner

Primary Examiner—Xu Mei
(74) Attorney, Agent, or Firm—Fish & Richardson P.C.

(57) ABSTRACT

A module adapted for use in a noise reduction headset earcup has an enclosure having walls separating an interior of the enclosure from an exterior of the enclosure outside the earcup. There is a driver with a diaphragm. A port connects the interior and exterior. An acoustically resistive opening connects the interior and exterior in parallel with the port.

9 Claims, 9 Drawing Sheets

FIG. 7

NOISE REDUCING

CROSS-REFERENCE TO RELATED APPLICATIONS

This application is a continuing application of application Ser. No. 08/843,985 filed Apr. 17, 1997 now abandoned, for ACOUSTIC NOISE REDUCING of Roman Sapiejewski.

BACKGROUND

For background, reference is made to U.S. Pat. Nos. 4,644,581, 4,922,542 and 5,305,387.

It is an important object of the invention to provide an improved noise reducing headset that may include active noise reduction.

BRIEF SUMMARY OF THE INVENTION

According to the invention, a module in a noise reduction headset includes an enclosure having walls. A driver is mounted in one of the walls. A port and a resistive opening in parallel intercouples the interior and exterior of the enclosure. The headset includes an earcup enclosing first and second cavities separated by a divider. The headset further includes a circumaural sealing pad constructed and arranged to effectively seal the first cavity to the head of a person.

In a specific aspect of the invention, for active noise reduction, a microphone is located in the first cavity adjacent to the driver.

Other features, objects and advantages of the invention will become apparent from the following detailed description when read in connection with the accompanying drawing in which:

DETAILED DESCRIPTION OF THE INVENTION

Figure 1:
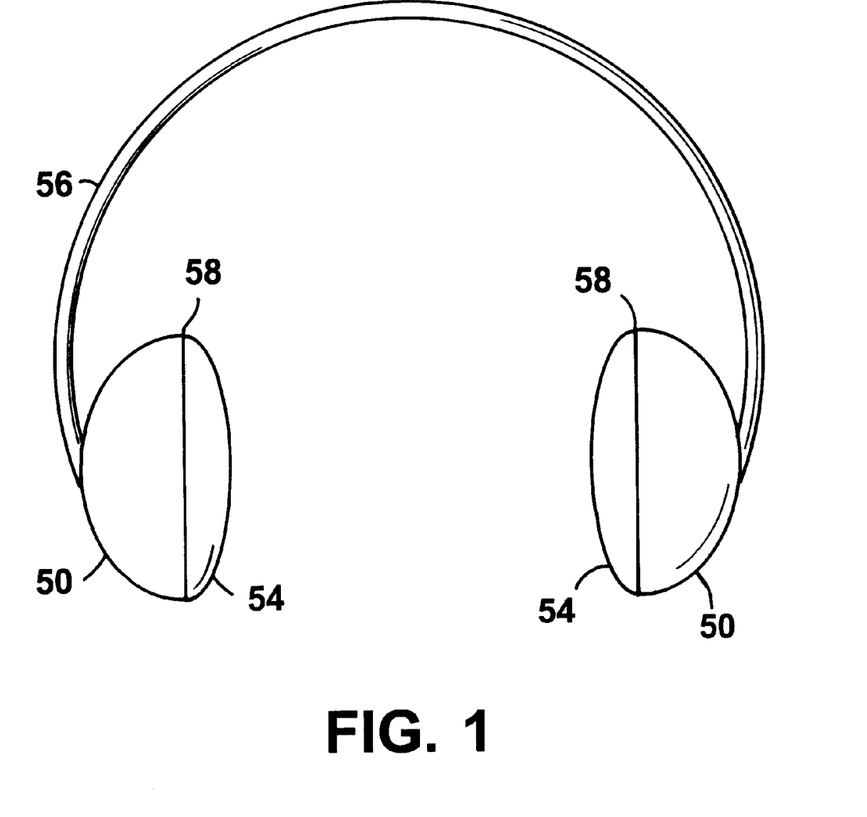
FIG. 1 is a plan view of a noise reduction headset.

With reference now to the drawing and more particularly to FIG. 1, there is shown an active noise reduction headset according to the invention. A headband 56 is attached to two earcup assemblies 58. Each of the earcup assemblies 58 includes an earcup portion 50 and a conformable pad 54. The headband can be one of many types, including headbands in which the length of the headband or the position of the earcup assemblies on the headband can be adjusted. The connection between the headband 56 and the earcup assemblies may allow for adjustment along one or more axes relative to the headband. In use, the headband 56 holds the earcup assemblies 58 over the user's ears, either enclosing the ear (circumaural) or over the ear (supraural).

Figure 2A:
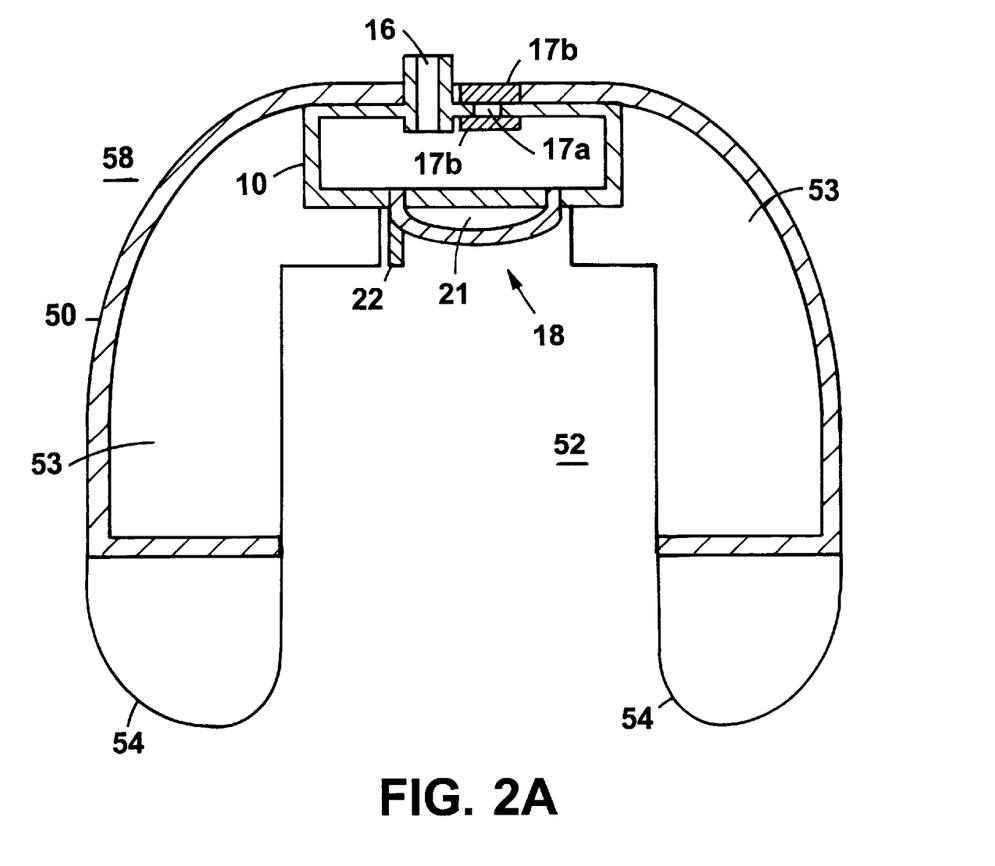
FIGS. 2A–2C are diagrammatic cross-sectional views of earcups employing the invention.
Figure 2B:
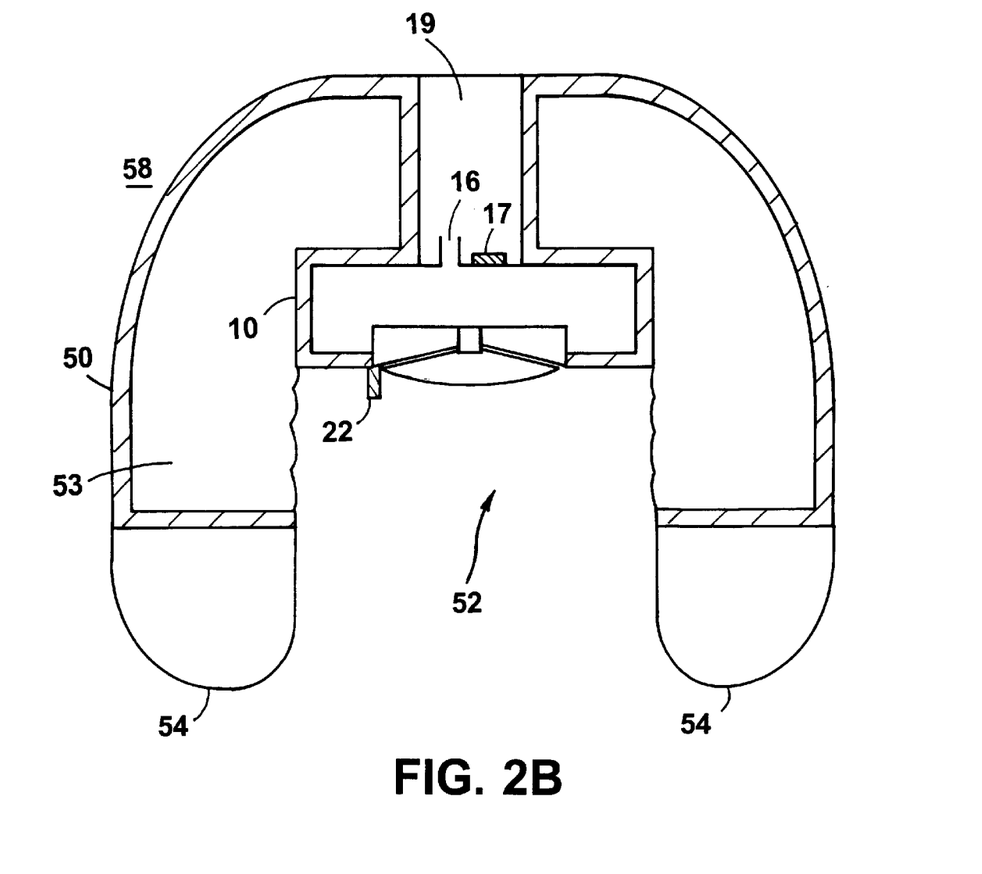
Figure 2C:
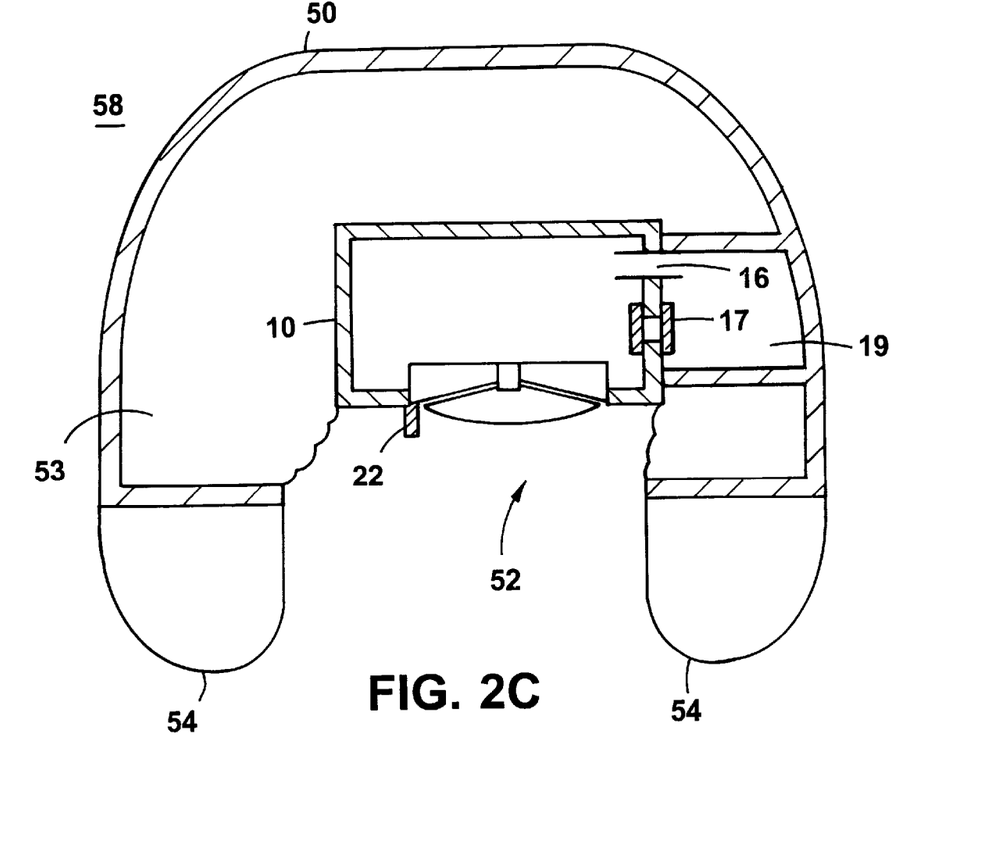

Referring to FIGS. 2A–2C, there are shown diagrammatic cross-sectional views of the earcup assembly 58. In FIG. 2A, earcup shell 50 encloses a front cavity 52. Conformable pads 54 seal against the side of the user's head so that they seal a user's ears from a substantial portion of the ambient noise. Front cavity 52 encloses active noise reduction module 10. Active noise reduction module 10 includes driver 18 which includes sound wave radiating diaphragm 21. Passing through earcup shell 50 are port 16 and acoustically resistive opening 17 in parallel which will be described in more detail below. In FIGS. 2B and 2C, passageway 19 connects port 16 and resistive opening 17 to the ambient environment. The dimensions of the passageway 19 are such that the passageway acts neither as a port nor a waveguide for sound waves radiated by diaphragm 21; the acoustic effect is the same as if the port 16 and the resistive opening 17 both connect directly to the ambient environment as in FIG. 2A. In front cavity 52 may be placed damping material 53 (for example, open cell foam) to reduce resonances in the front cavity and assist in passive attenuation. An embodiment as in FIGS. 2B and 2C is advantageous, because it allows flexibility in the placement of the active noise reduction module, and it makes the active noise reduction module 10 implementable in a variety of different earcups with minimal modification to the earcup.

In operation, microphone 22 measures sound pressure. Circuitry (not shown) compares sound pressure measured by microphone 22 with sound pressure due to sound waves radiated by diaphragm 21 to detect ambient noise, and transmits to driver 18 signals which cause diaphragm 21 to radiate sound patterns similar to the ambient noise, but out of phase with ambient noise, thereby significantly attenuating it.

Figure 3A:
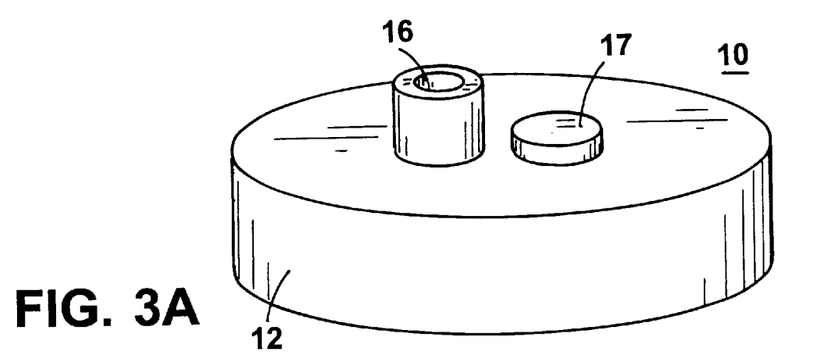
FIGS. 3A and 3B are perspective views of a module according to the invention.
Figure 3B:
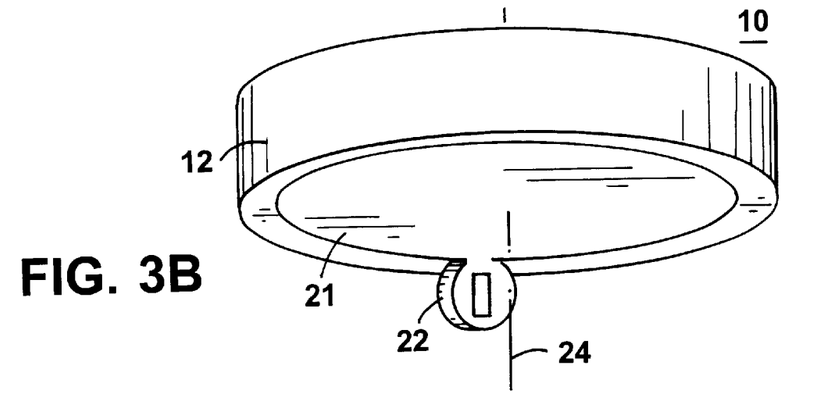
Figure 4A:
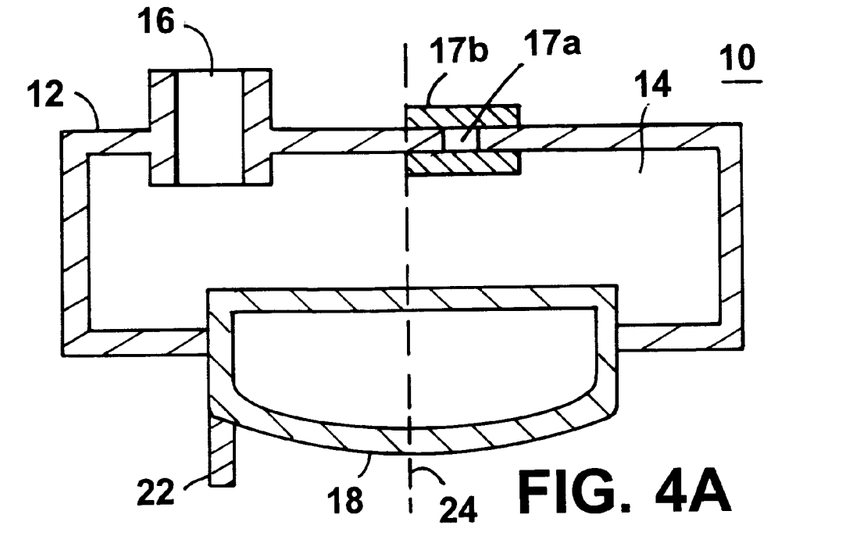
FIGS. 4A–4C are cross-sectional views of alternate embodiments of a module according to the invention.
Figure 4B:
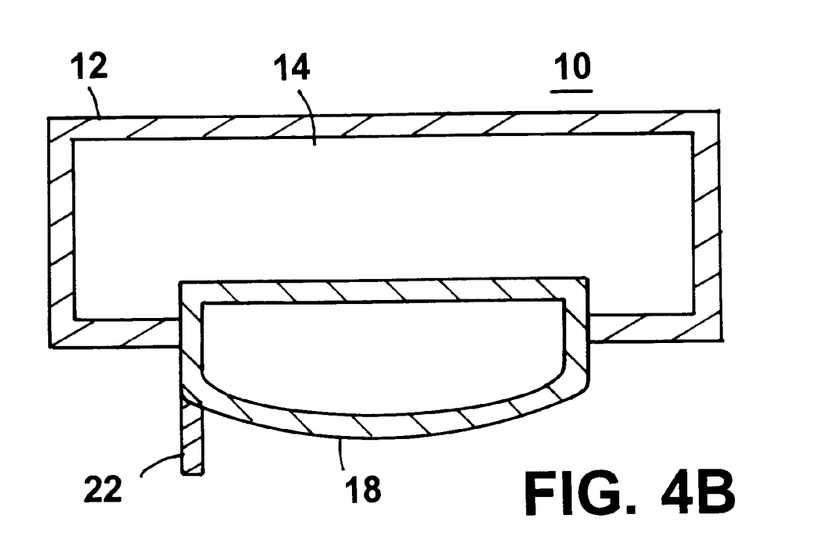
Figure 4C:
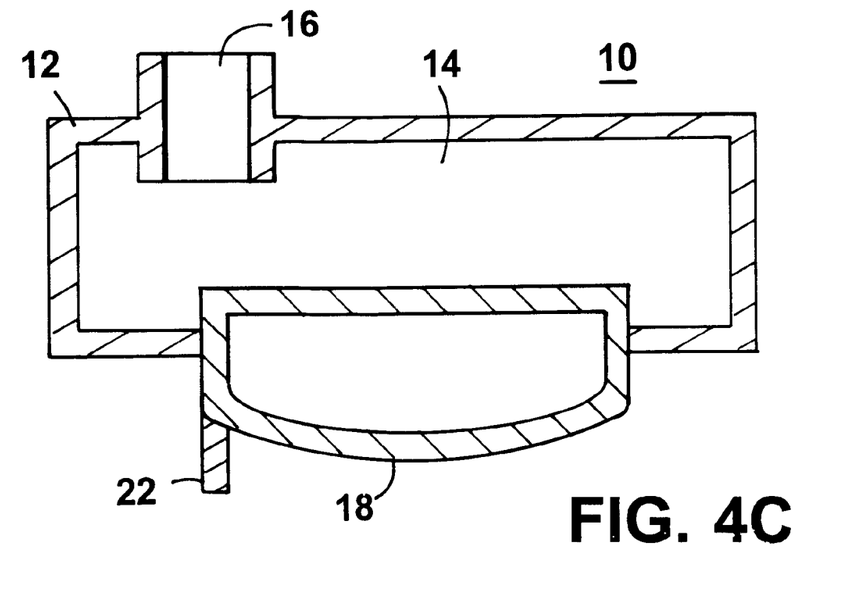

Referring to FIGS. 3A–3B, there are shown views of active noise reduction module 10. An enclosure 12 encloses a back cavity 14 (FIGS. 4A–4C). Passing through a wall of enclosure 12 are port 16 and acoustically resistive opening 17. Mounted in a surface of enclosure 12 is driver 18. Microphone 22 is mounted on the exterior of enclosure 12. In this embodiment, microphone 22 is mounted at a position approximately at the edge of diaphragm 21, with the pickup surface facing radially inwardly; that is, such that a line perpendicular to the pickup surface is approximately orthogonal to the axis 24 of driver 18.

In one embodiment of the invention, enclosure 12 is generally cylindrical, with driver 18 being approximately 42 mm in diameter and mounted in one of the planar surface of the cylinder. Back cavity 14 enclosed by enclosure 12 has a volume of typically approximately 10 to 20 cubic centimeters, and front cavity 52 adapted to engage the ear of the user typically has a volume of about 100–200 cubic centimeters so that the volume of back cavity 14 is significantly less than the volume of front cavity 52. The acoustic mass of port 16 and compliance of back cavity 14 are typically tuned to a frequency of about 300 Hz. Acoustically resistive opening 16 provides an acoustic resistance of about 1×167 ohms. Resistive opening 17 may be an opening 17a with an acoustically resistive covering 17b, or may be an opening filled with acoustically resistive material.

Referring now to FIGS. 4A–4C, there are shown the active noise reduction module 10 with certain elements omitted or modified to better explain the invention. FIGS. 4B–4D will be used below to explain the effect of some of the features of the embodiment of FIG. 4A. In FIG. 4B, port 16 and resistive opening 17 are omitted. In FIG. 4C, resistive opening 17 is omitted.

In the embodiment of FIG. 4A, the acoustic resistance of the resistive opening 18 connects back cavity 14 with ambient environment in parallel with the mass of the air in port 16.

Figure 5:
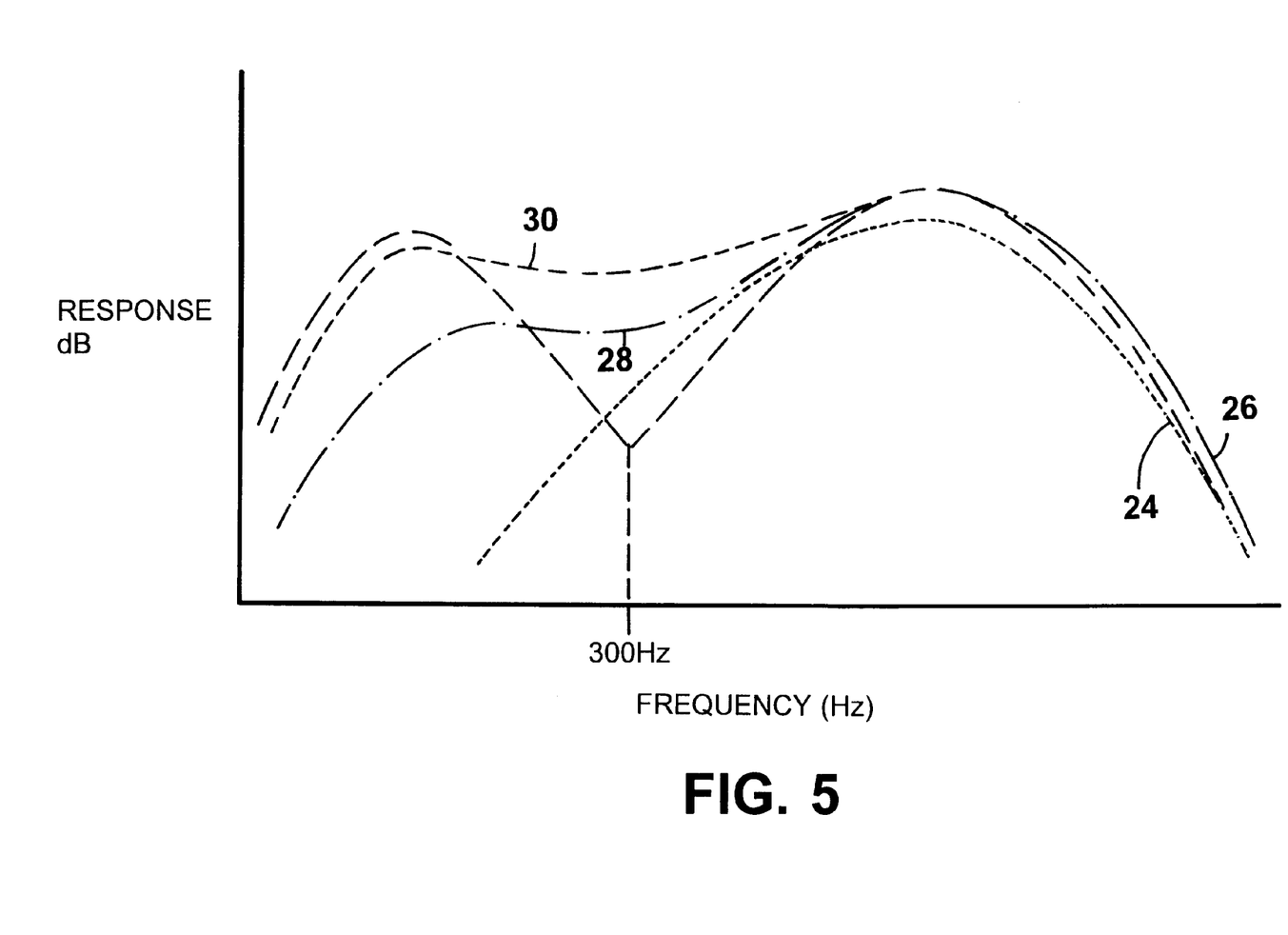
FIG. 5 is a plot of driver response vs. frequency for the modules of FIGS. 4A–4C.

Referring now to FIG. 5, there is shown plots of a computer simulation of the response of driver 18 as a function of frequency, illustrating the effect of various elements of the embodiment of FIG. 3A. Curve 24 represents the response of driver 18 in the embodiment of FIG. 4B. Curve 26 represents the response of driver 18 in the embodiment as shown in FIG. 4C. As compared with curve 24, curve 26 shows better response at lower frequencies, but also has low output at the port resonance frequency, in this case 300 Hz. Curve 30 represents the response of the embodiment of FIG. 4A. As compared with curves 24, 26 and 28, curve 30 shows smooth frequency response and improved response at low frequencies.

An earcup according to the invention is advantageous over conventional earcups because the port and resistive path configuration allows active attenuation to be attained with a significantly smaller back cavity. This feature, in turn, allows for a given earcup size, a larger front cavity, which improves passive attenuation. The smooth frequency response facilitates using simpler electronic circuitry, and combined with the more efficient operation of the driver, allows for significantly reduced power consumption, a particular advantage in battery-powered active noise reduction headsets.

Figure 6:
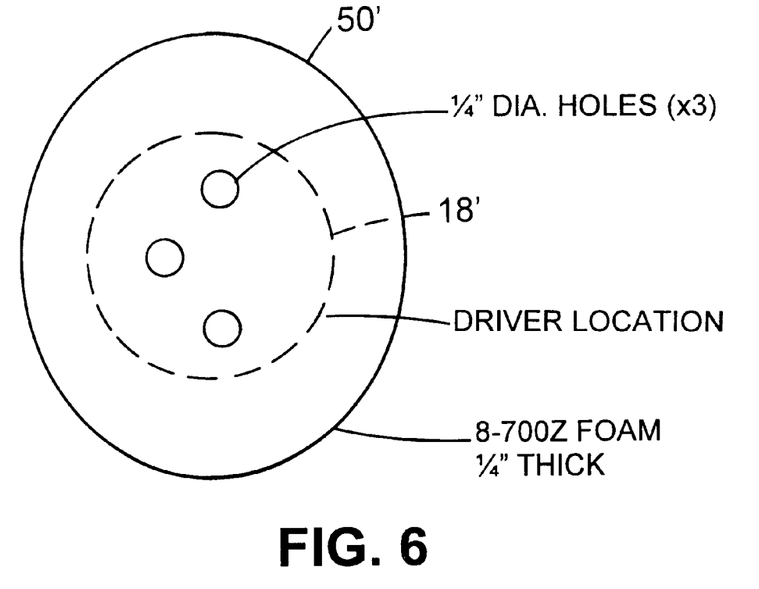
FIG. 6 is a diagrammatic plan view of the open end of a cup in a passive headset according to the invention.
Figure 7:
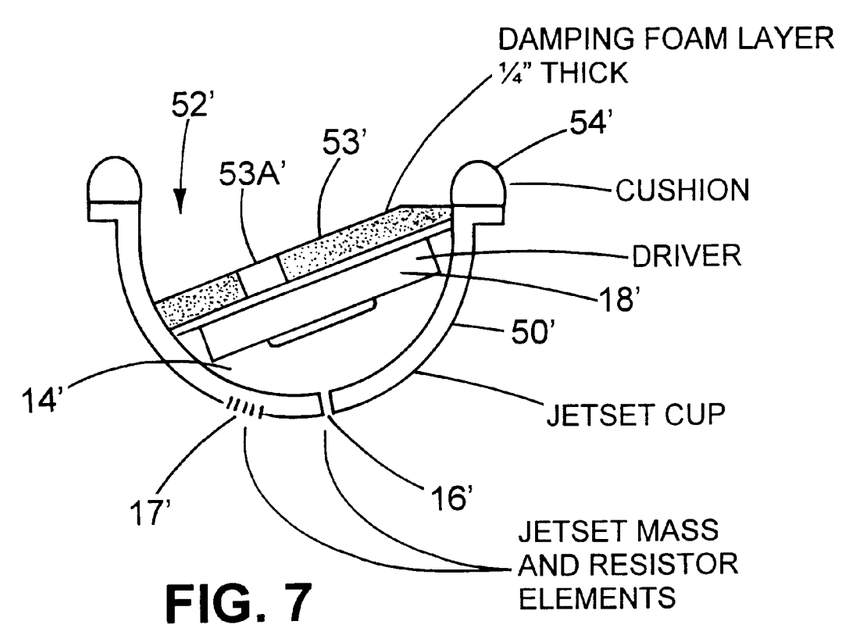
FIG. 7 is a diagrammatic sectional view of the cup of FIG. 6.

Referring to FIGS. 6 and 7, there are shown diagrammatic plan and sectional views, respectively, of an earcup in a passive headset according to the invention. Earcup shell 50' carries driver 18' covered by damping foam layer 53' typically ¼" thick of 8-700Z foam formed with openings 53A' in the front cavity 52' with circumaural cushion 54' constructed and arranged to effect a good seal against the side of the user's head around the user's ears. Port 16' and resistive opening 17' couple rear cavity 14' to the ambient environment outside cup 50'. There are three openings 53A' in damping foam layer 53' as shown in FIG. 6, only one of which is visible in the sectional view of FIG. 7. As can be seen from the drawing, the driver with a diaphragm mounted in the divider between the front and back cavity coacts therewith to prevent airflow between the back cavity and the front cavity.

The invention provides passive attenuation by surrounding the ear with a cavity that is effectively sealed to the head. By using the port 16' and resistive opening 17' structure according to the invention, rear cavity 14' is effectively opened to the ambient region outside at low frequencies, but remains sealed at mid and high frequencies to effectively increase low frequency output of driver 18' with little effect on the overall passive attenuation. The arrangement of foam 53' with openings 53A' positioned in front of the driver 18' in front cavity 52' improves frequency response to provide passive equalization.

It is evident that those skilled in the art may now make numerous uses and modifications of and departures from the specific apparatus and techniques herein disclosed without departing from the inventive concepts. Consequently, the invention is to be construed as embracing each and every novel feature and novel combination of features present in or possessed by the apparatus and techniques herein disclosed.

What is claimed is:

1. A noise reduction headset comprising,
    an earcup enclosing a back cavity having a compliance and a front cavity,
    the volume of said back cavity being significantly less than the volume of said front cavity,
    said front cavity adapted to engage the ear of a user,
    a divider,
    a driver with a diaphragm mounted in said divider and coacting therewith to prevent airflow between said front cavity and said back cavity,
    a port connecting said back cavity with the exterior outside said earcup,
    said port having a mass that coacts with said compliance to establish a resonant circuit having a resonance at a resonant frequency, and
    an acoustically resistive opening connecting said back cavity and said exterior in parallel with said port.

2. A noise reduction headset in accordance with claim 1, further comprising a microphone having a pickup surface,
    said microphone mounted at approximately an outer edge of said diaphragm.

3. A noise reduction headset in accordance with claim 2, wherein a pickup surface of said microphone is oriented perpendicularly to an axis of said driver.

4. A noise reduction headset in accordance with claim 2, wherein a pickup surface of said microphone faces radially inward.

5. A noise reduction headset in accordance with claim 1, wherein said rear cavity has a volume of about 10–20 cc and said front cavity has a volume of about 100–200 cc.

6. A noise reduction headset comprising,
    an earcup, enclosing a first cavity and a second cavity having compliance,
    the volume of said second cavity significantly less than the volume of said first cavity,
    said first cavity and said second cavity separated by a divider,
    a conformable pad constructed and arranged to seal said earcup from a side of a head of a user,
    a driver having a diaphragm mounted in said divider and coacting therewith to prevent airflow between said first cavity and said second cavity,
    a port connecting said second cavity and the region outside said earcup,
    said port having a mass that coacts with the second cavity compliance to establish a resonant circuit, and
    an acoustically resistive opening connecting said second cavity and the region outside said earcup in parallel with said port.

7. An active noise reduction headset in accordance with claim 6, further comprising a microphone in said first cavity.

8. An active noise reduction headset in accordance with claim 7, wherein said microphone is mounted at approximately an outer edge of said diaphragm.

9. A noise reduction headset in accordance with claim 6, wherein said divider comprises a wall of a module,
    said module enclosing said second cavity,
    said module being adapted to be removably integrated into said earcup in such a manner that said port and said acoustically resistive opening connect said second cavity and said region through an opening in said earcup.

* * * * *